(12) United States Patent
Fujikake et al.

(10) Patent No.: US 11,071,639 B2
(45) Date of Patent: Jul. 27, 2021

(54) BRACE AND INSERTION-FITTING MEMBER USED THEREFORE

(71) Applicant: TOYOTA JIDOSHA KABUSHIKI KAISHA, Toyota (JP)

(72) Inventors: Yoshinori Fujikake, Nagakute (JP); Yasuki Kato, Nagoya (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 477 days.

(21) Appl. No.: 15/935,664

(22) Filed: Mar. 26, 2018

(65) Prior Publication Data

US 2018/0289523 A1    Oct. 11, 2018

(30) Foreign Application Priority Data

Apr. 11, 2017  (JP) .............................. JP2017-078543

(51) Int. Cl.
*A61F 5/01* (2006.01)
(52) U.S. Cl.
CPC .... *A61F 5/0127* (2013.01); *A61F 2005/0155* (2013.01); *A61F 2005/0158* (2013.01);
(Continued)
(58) Field of Classification Search
CPC ............................ A61H 3/00; A61H 2201/165
(Continued)

(56) References Cited

U.S. PATENT DOCUMENTS 3,945,389 A * 3/1976 Smith ...................... A61H 3/00
135/67
4,353,361 A   10/1982 Foster
(Continued)

FOREIGN PATENT DOCUMENTS

DE  10 2013 011 382 A1   1/2015
JP      5-137742 A        6/1993
(Continued)

OTHER PUBLICATIONS

U.S. Final Office Action issued in U.S. Appl. No. 15/936,702 dated Sep. 30, 2020.
(Continued)

*Primary Examiner* — Rachael E Bredefeld
*Assistant Examiner* — Trisha Talapatra
(74) *Attorney, Agent, or Firm* — Oblon, McClelland, Maier & Neustadt, L.L.P.

(57) ABSTRACT

A brace includes a first member, a second member, a joint mechanism, and an insertion-fitting member configured to be insertion-fitted into the joint mechanism in such a manner that the insertion-fitting member can be fixed to and removed from the joint mechanism; the joint mechanism includes an insertion-fitting receiving part, the insertion-fitting receiving part being configured to enable the insertion-fitting member to be insertion-fitted into the joint mechanism, and a regulation part being disposed around the rotation axis in the second member; and the regulation part, which rotates around the rotation axis in an integrated manner with a rotation of the second member, comes into contact with the insertion-fitting member fixed to the insertion-fitting receiving part on a trajectory of the rotation of the regulation part, so that a range of the rotation of the second member is regulated.

8 Claims, 12 Drawing Sheets

(52) U.S. Cl.
CPC .................. *A61F 2005/0165* (2013.01); *A61F 2005/0167* (2013.01); *A61F 2005/0169* (2013.01)

(58) Field of Classification Search
USPC ........................ 602/16, 5, 9, 12, 26, 27, 22
See application file for complete search history.

(56) References Cited

U.S. PATENT DOCUMENTS

| | | | | |
|---|---|---|---|---|
| 5,372,574 | A * | 12/1994 | Hino | ................. A61F 5/0102 16/342 |
| 5,772,619 | A | 6/1998 | Corbett | |
| 8,491,511 | B2 * | 7/2013 | Gentz | ................. A61F 5/0127 602/16 |
| 10,555,829 | B2 * | 2/2020 | Lurssen | ................. A61F 5/0125 |
| 2003/0091382 | A1 | 5/2003 | Kowalsky et al. | |
| 2004/0015112 | A1 | 1/2004 | Salutterback et al. | |
| 2004/0127825 | A1 | 7/2004 | Castillo et al. | |
| 2009/0137934 | A1 | 5/2009 | Seon | |
| 2011/0009788 | A1 | 1/2011 | Kelly et al. | |
| 2012/0035520 | A1 | 2/2012 | Ingimundarson et al. | |
| 2012/0041348 | A1 | 2/2012 | Maekita | |
| 2012/0059296 | A1 | 3/2012 | Kompa | |
| 2016/0151190 | A1 | 6/2016 | Lurssen | |
| 2016/0361189 | A1 * | 12/2016 | Campbell | ............. A61F 5/0125 |

FOREIGN PATENT DOCUMENTS

| | | |
|---|---|---|
| JP | 2007-54086 | 3/2007 |
| JP | 4998623 | 8/2012 |
| JP | 2016-83100 A | 5/2016 |
| WO | WO 2011/129013 A1 | 10/2011 |
| WO | 20161121019 A1 | 8/2016 |

OTHER PUBLICATIONS

Office Action dated Apr. 29, 2020 in co-pending U.S. Appl. No. 15/936,702, 14 pages.
U.S. Advisory Action issued in U.S. Appl. No. 15/936,702 dated Jan. 13, 2021.

* cited by examiner

BRACE AND INSERTION-FITTING MEMBER USED THEREFORE

CROSS REFERENCE TO RELATED APPLICATIONS

This application is based upon and claims the benefit of priority from Japanese patent application No. 2017-78543, filed on Apr. 11, 2017, the disclosure of which is incorporated herein in its entirety by reference.

BACKGROUND

The present disclosure relates to a brace and an insertion-fitting member used therefore.

An assistance brace that is attached to a leg of a user and assists walking of the user has been known. For example, in an assistance brace disclosed in Japanese Unexamined Patent Application Publication No. 2007-54086, a lower-thigh frame attached to a lower thigh of a user is rotatably connected to a sole frame on which the user places his/her sole. In this assistance brace, assisting motions are controlled by driving a link mechanism by using a motor so that a plantar-flexion/dorsiflexion motion of an ankle joint is assisted and the plantar-flexion/dorsiflexion motion of the ankle joint does not exceed a movable range.

SUMMARY

The present inventors have found the following problem. A power-driven assistance brace tends to have a large size and hence its usability as a brace used for a joint of a human body including an ankle joint is not satisfactory. Even in the case of a passive assistance brace that does not provide power-driven assistance to joint motions, depending on a state of a disease of a user, it is necessary to regulate a movable range of the assistance brace so that the user does not excessively bend his/her joint. However, when a regulation range within which a user is allowed to bend his/her joint is made narrower than a range within which the user can physically and naturally bend the joint, a large impact is given to a regulation member at both ends of the regulated range by a bending force of the joint. When the regulation member is damaged or worn out by such impacts, it becomes impossible to appropriately manage the allowable motion range and, in some cases, such damage interferes with a rehabilitation plan.

The present disclosure has been made to solve the above-described problem and an object thereof is to provide a brace capable of accurately and easily maintaining a movable range of a joint within a desired regulation range and an insertion-fitting member used therefore.

A first exemplary aspect is a brace including: a first member configured to be attached to a part of a body located along a first bone part of a wearer; a second member configured to be attached to a part of a body located along a second bone part of the wearer; and a joint mechanism configured to support the first and second members so that the first and second members can rotate with respect to each other around a rotation axis, in which the brace further includes an insertion-fitting member configured to be insertion-fitted into the joint mechanism in such a manner that the insertion-fitting member can be fixed to and removed from the joint mechanism, the joint mechanism includes: an insertion-fitting receiving part integrally provided with the first member, the insertion-fitting receiving part being configured to enable the insertion-fitting member to be insertion-fitted into the joint mechanism; and a regulation part integrally provided with the second member, the regulation part being disposed around the rotation axis in the second member, and the regulation part, which rotates around the rotation axis in an integrated manner with a rotation of the second member, comes into contact with the insertion-fitting member fixed to the insertion-fitting receiving part on a trajectory of the rotation of the regulation part, so that a range of the rotation of the second member is regulated.

By regulating the rotation range of the regulation part by using the insertion-fitting member which is insertion-fitted in a replaceable manner as described above, it is possible to replace the insertion-fitting member with a new one when it is worn out or damaged. Therefore, it is possible to accurately regulate the movable range of the joint to a target range. Consequently, it is possible to carry out a rehabilitation plan without a hitch.

In the above-described configuration, the insertion-fitting member, which is insertion-fitted into the insertion-fitting receiving part, is selected from a set of a plurality of insertion-fitting members according to a desired regulated rotation range, the plurality of insertion-fitting members including projecting parts having projecting lengths different from each other. By preparing insertion-fitting members having different projecting lengths, it is possible to easily change the desired regulated rotation range according to a wearer's situation.

Further, the insertion-fitting member may be able to be insertion-fitted into the insertion-fitting receiving part in a state in which the first and second members are already attached to the wearer. By configuring the brace in the above-described manner, it is possible, when the insertion-fitting member is worn out or damaged, to replace the insertion-fitting member with a new one without detaching the joint regulation apparatus from the wearer, even when the wearer is doing rehabilitation training.

Further, the insertion-fitting member can be configured so as to include: a first insertion-fitting member including a first projecting part configured to come into contact with the regulation part at one end of a rotating motion thereof; and a second insertion-fitting member including a second projecting part configured to come into contact with the regulation part at the other end of the rotating motion thereof. Note that the projecting length of the first projecting part may be made different from the projecting length of the second projecting part. By adopting the configuration in which the regulation part is regulated at one end and the other end thereof by using different insertion-fitting members as described above, it is possible to replace these insertion-fitting members separately from each other according to their worn-out states or the like. Further, by using insertion-fitting members having different projecting lengths, it is possible, when the joint regulation apparatus is applied to, for example, an ankle joint, to adjust a movable range for plantar-flexion and a movable range for dorsiflexion separately from each other.

Further, the projecting part of the insertion-fitting member preferably projects in a direction perpendicular to the rotation axis of the regulation part, and a contact part of the regulation part, which comes into contact with the projecting part, preferably forms a cylindrical-surface shape so as to come into contact with the projecting part in a straight line parallel to the rotation axis. By configuring the brace in the above-described manner, since the regulation part and the insertion-fitting member make line-contact with each other, it is possible to disperse the impact force caused by the collision.

Further, the insertion-fitting member can be configured so as to include a locking part configured to be locked in the insertion-fitting receiving part when the insertion-fitting member is inserted into the insertion-fitting receiving part and then rotated around a rotation axis parallel to an insertion-fitting direction. By providing the above-described locking part, it is possible to disperse the impact force, which is originally exerted on the insertion-fitting member, to the insertion-fitting receiving part. Further, it is possible to prevent the insertion-fitting member from being accidentally removed. In this case, the joint mechanism preferably includes a positioning mechanism for stopping the insertion-fitting member in a predetermined phase when the insertion-fitting member is rotated. By providing the positioning mechanism, it is possible to position the insertion-fitting member at a more accurate position.

Further, one of the first and second members is preferably a lower-thigh frame attached to a lower thigh of the wearer, and the other of the first and second members is preferably a sole plate on which the wearer places his/her sole. Further, the joint mechanism is preferably used in such a manner that the rotation range is determined so that a range of a plantar-flexion motion and a dorsiflexion motion of an ankle joint of the wearer is regulated. In the regulation for motions of an ankle joint, large impacts tend to occur particularly at both ends of the regulation range and hence a number of advantageous effects can be enjoyed by the above-described function which enables the insertion-fitting member to be replaced.

According to the present disclosure, it is possible to provide a joint regulation apparatus capable of accurately and easily maintaining a movable range of a joint in a desired regulation range and a regulation member used therefore.

The above and other objects, features and advantages of the present invention will become more fully understood from the detailed description given herein below and the accompanying drawings which are given by way of illustration only, and thus are not to be considered as limiting the present invention.

DESCRIPTION OF EMBODIMENTS

The present disclosure is explained hereinafter by using embodiments. However, the present disclosure according to the claims is not limited to the below-shown embodiments. Further, each of the components explained in the embodiments is not necessarily indispensable as means for solving the problem.

Figure 1:
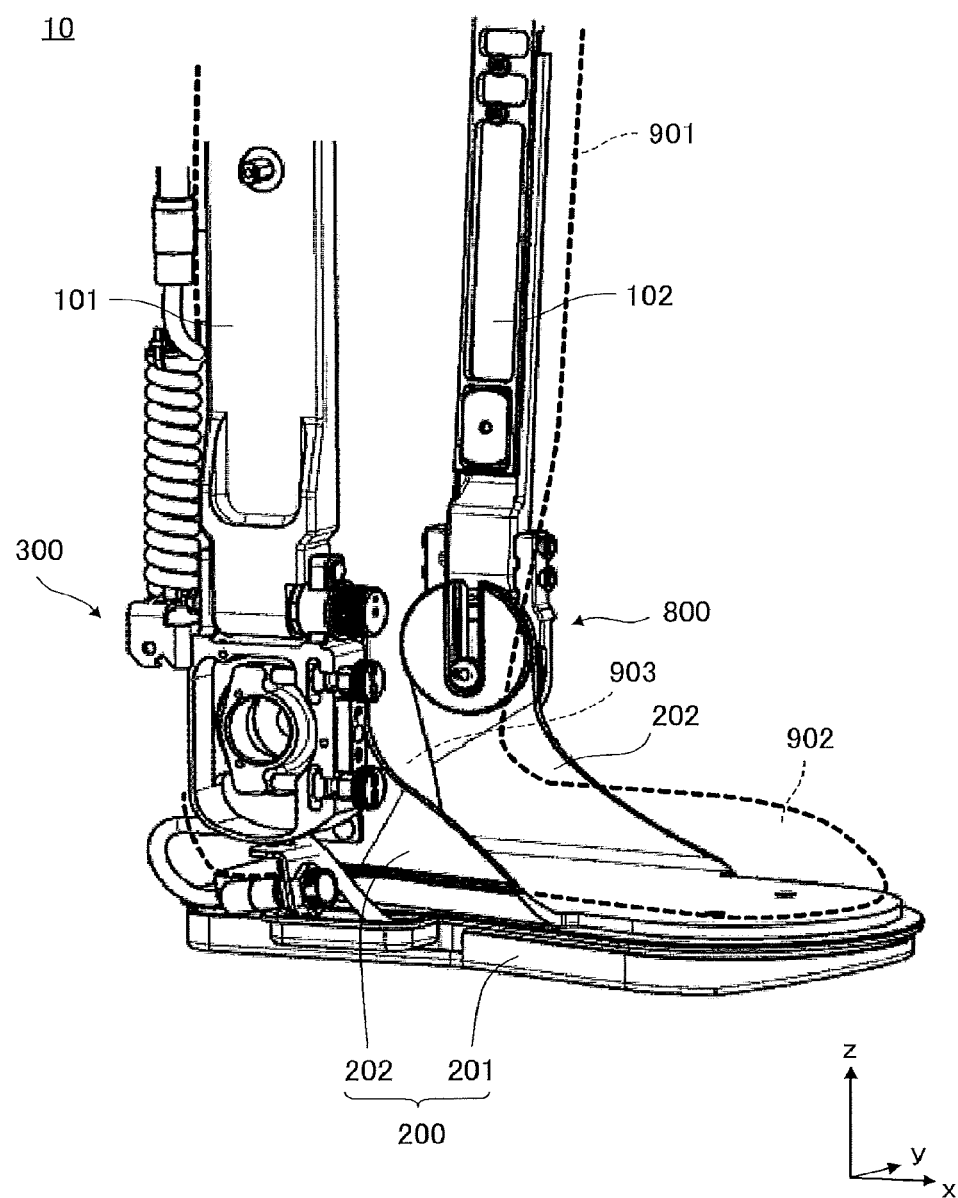
FIG. 1 is a perspective view of an external appearance of an ankle joint regulation apparatus according to an embodiment.

FIG. 1 is a perspective view of an external appearance of an ankle joint regulation apparatus 10 according to an embodiment. The ankle joint regulation apparatus 10 is a regulation apparatus that regulates a movable range of an ankle joint 903 that connects a bone of a calf area (i.e., a shinbone and a fibula) of a wearer with his/her anklebone. The ankle joint regulation apparatus 10 is mainly composed of a calf area frame 101 that is located on a side of a calf area bone and supports a calf area 901, a sole frame 200 that is located on a side of the anklebone and supports a part from an ankle to a tip of a foot 902, and a joint mechanism 300 that supports these two frames so that they can swing within a swing range regulated along a movable direction of the ankle joint 903.

The sole frame 200 includes a bottom plate 201 having a placement surface on which the wearer places his/her sole, and side plates 202 vertically disposed on sides of the bottom plate 201. More specifically, the joint mechanism 300 connects a lower end of the calf area frame 101 with the outer-side side plate 202 in such a manner that they can swing. The sole frame 200 is attached to the foot 902 through an attachment belt or the like (not shown). For example, when the wearer wears a shoe-like cup sole, the sole frame 200 may be constructed so as to fix the cup sole. As described later, the joint mechanism 300 has such a structure that the joint mechanism 300 swings within a range that is narrower than a range within which the ankle joint 903 can be physically and naturally bent. Note that FIG. 1 shows a state in which a cover of the joint mechanism 300 (which is described later) is removed in order to clarify relations between components/structures shown in FIG. 1 and those shown in the subsequent drawings.

The ankle joint regulating apparatus 10 further includes a calf area frame 102 located on a side of the calf area 901 opposite to the side on which the lower-thigh frame 101 is located. That is, the calf area frames 101 and 102 are attached so as to sandwich the calf area 901 therebetween and support the calf area 901. Note that the calf area frames 101 and 102 are attached to the calf area 901 through an attachment belt or the like (not shown).

The ankle joint regulating apparatus 10 includes a connecting mechanism 800 that connects the calf area frame 102 with the inner-side side plate 202 in such a manner that they can swing. Unlike the joint mechanism 300, the connecting mechanism 800 does not include a structure for regulating the swing. That is, the movable range of the ankle joint 903 is not regulated by the connecting mechanism 800 located on the inner side thereof, but is instead regulated by the joint mechanism 300 located on the outer side thereof. By adopting the above-described structure, the regulation range can be conveniently adjusted without detaching the ankle joint regulating apparatus 10 from the wearer.

Note that in FIG. 1, it is assumed that the diseased leg is the right leg and a state in which the joint mechanism 300 is disposed on the outer side of the right leg is shown. In this embodiment, the ankle joint regulating apparatus 10 is a regulation apparatus for a right leg. However, needless to say, it is possible to manufacture a regulation apparatus for a left leg in which the joint mechanism 300 is disposed on the outer side of the left leg. Further, as shown in the figures, a direction from an ankle toward a toe is defined as a positive direction on an x-axis, and a direction toward the inner side on a plane (i.e., a surface) of the bottom plate 201 is defined as a positive direction on a y-axis. Further, a direction toward an upper body along the thigh is defined as a positive direction on a z-axis. The same coordinate system as that shown in FIG. 1 is shown in each of the subsequent drawings to clarify each direction.

Figure 2:
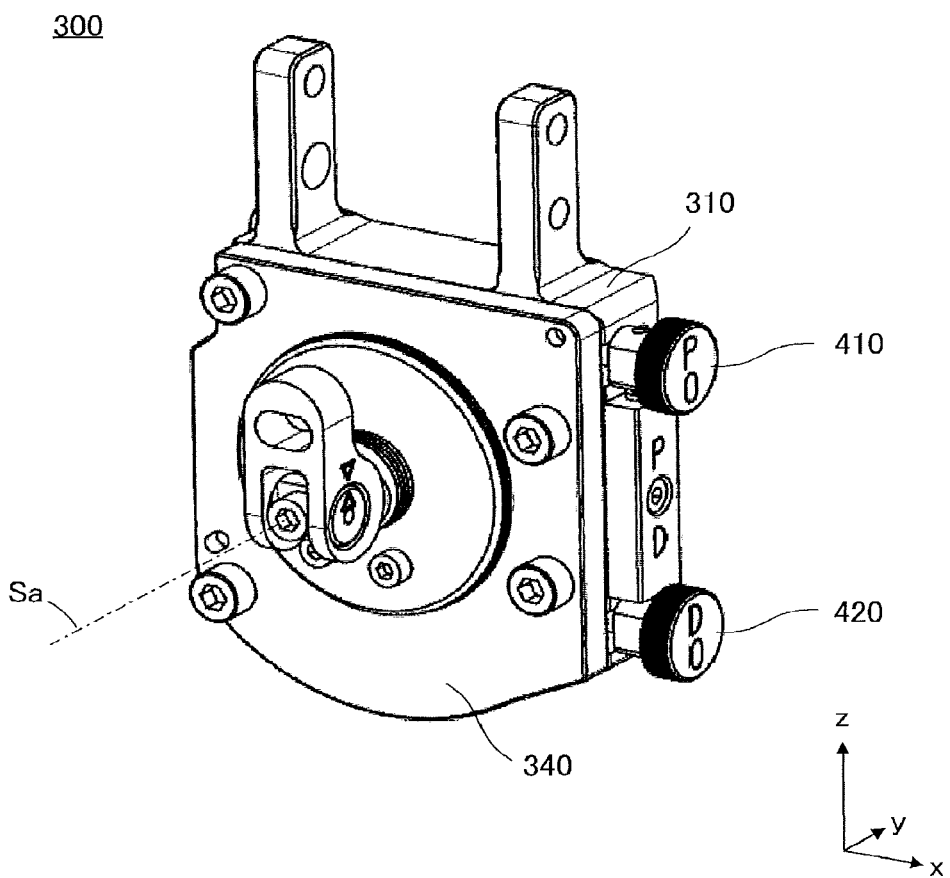
FIG. 2 is a perspective view of an external appearance of a joint mechanism.

FIG. 2 is a perspective view of an external appearance of the joint mechanism 300. In contrast to FIG. 1, FIG. 2 shows a state in which a cover 340 is attached. In actual use, the cover 340 is attached to the joint mechanism 300 in order to prevent dust and the like from entering into the mechanism as shown in the figure. The joint mechanism 300 includes a holder 310 and stopper pins 410 and 420 in addition to the cover 340. Note that the stopper pin 410 and the holder 310 are examples of the insertion-fitting member and the insertion-fitting receiving part, respectively.

The holder 310 is fixed to the calf area frame 101. The holder 310 is formed by, for example, carving it out of an aluminum block. Note that the holder 310 may be connected to the calf area frame 101 so that the holder 310 is allowed to slightly rotate around the x-axis with respect to the calf area frame 101. The stopper pins 410 and 420 are insertion-fitted into the holder 310 (i.e., fitted in the holder 310 by insertion) from a side thereof and thereby mounted in the joint mechanism 300. Specific structures are described later.

Figure 3:
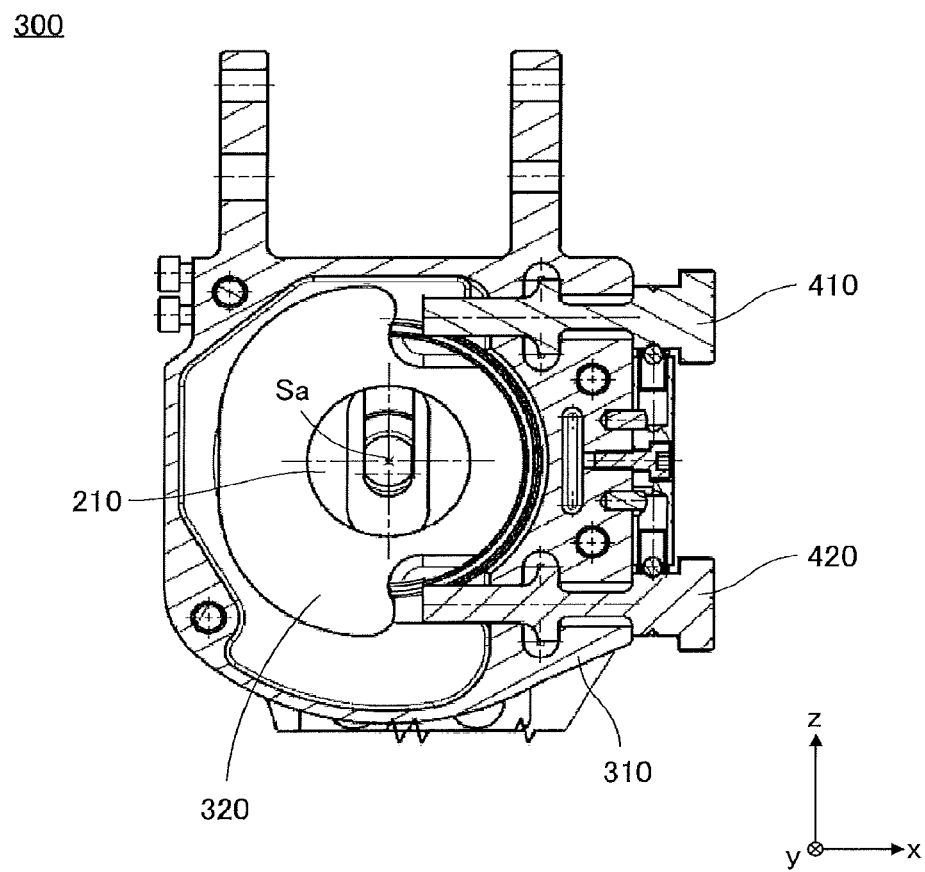
FIG. 3 is a cross section showing a configuration of a main part of the joint mechanism.

FIG. 3 is a cross section showing a configuration of a main part of the joint mechanism 300 when the holder 310 is cut on a plane parallel to the xz-plane. That is, FIG. 3 shows a state of an internal space of the holder 310. A swing shaft 320 is housed in the internal space of the holder 310. Note that the swing shaft 320 is an example of the regulation part.

The swing shaft 320 is fixed to the side plates 202 of the sole frame 200 through a coupling member 210. The swing shaft 320 is pivotally supported on the holder 310 in such a manner that it can swing around a swing axis Sa. That is, when the wearer performs a dorsiflexion motion and a plantar-flexion motion by moving his/her ankle joint, the sole frame 200 follows the motions and hence the swing shaft 320 swings around the swing axis Sa with respect to the holder 310.

The stopper pin 410 is insertion-fitted into the holder 310 from a side thereof and regulates, regarding the swing range of the swing shaft 320, the swing angle of the plantar-flexion motion. The stopper pin 420 is insertion-fitted into the holder 310 from the side thereof and regulates, regarding the swing range of the swing shaft 320, the swing angle of the dorsiflexion motion. Specific structures and specific motions are described later.

Figure 4:
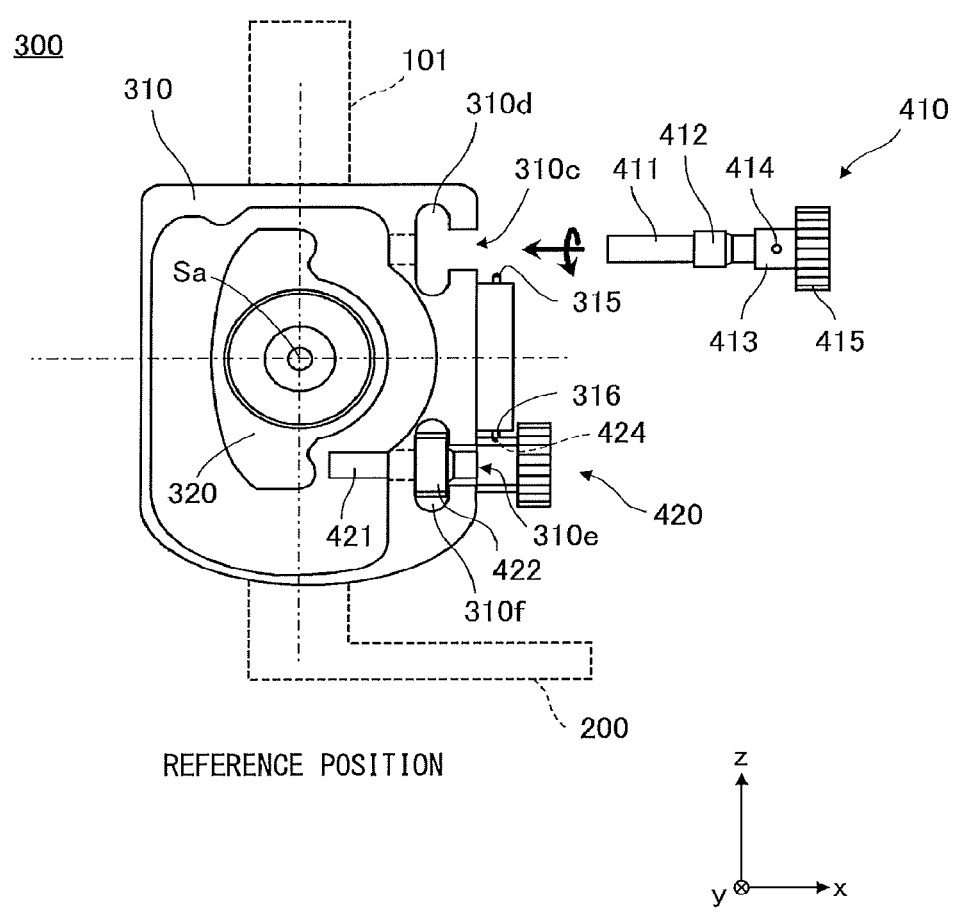
FIG. 4 is a schematic diagram schematically showing a reference state of the joint mechanism.
Figure 5:
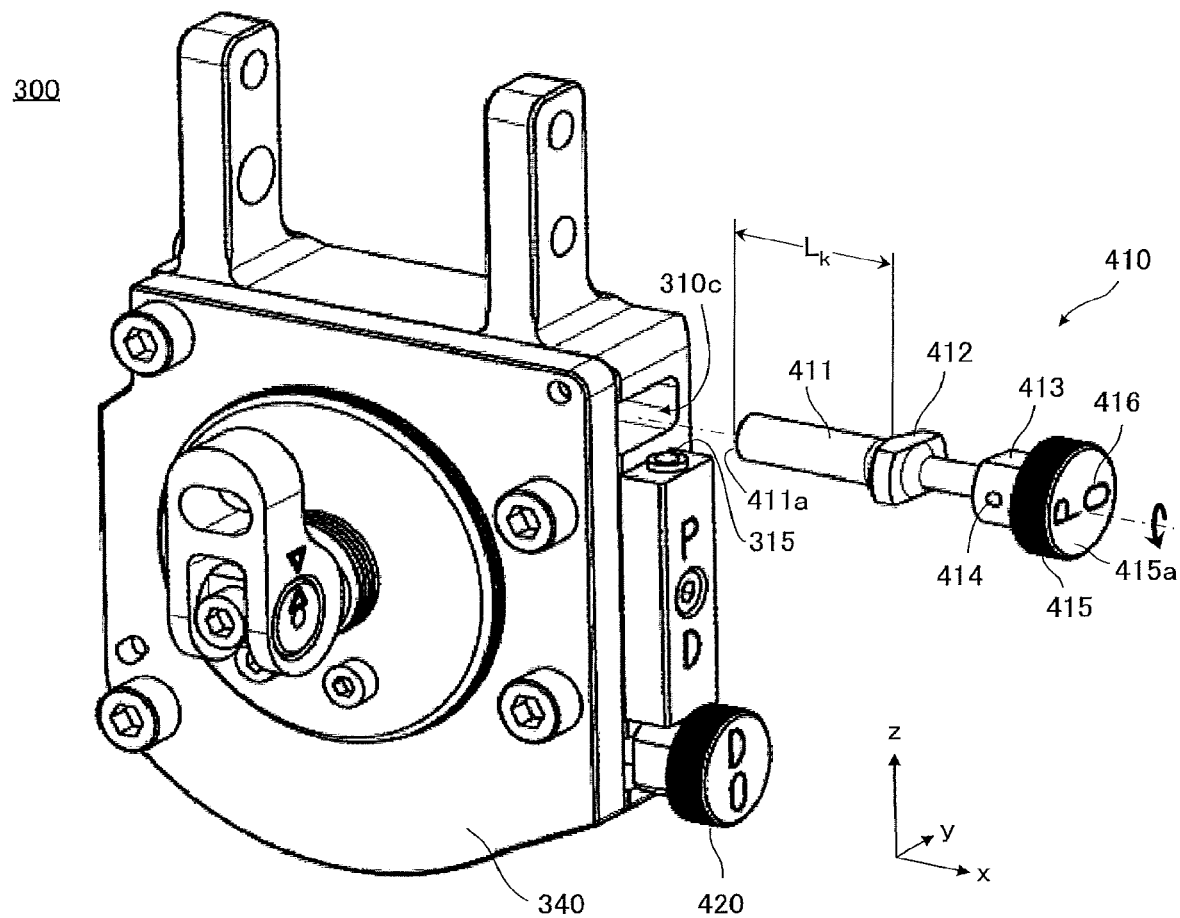
FIG. 5 is a perspective view of an external appearance of a state in which a stopper pin is insertion-fitted into a holder.

FIG. 4 is a schematic diagram schematically showing a reference state of the joint mechanism 300. Note that the reference state means a state in which the wearer stands upright. In this state, the sole frame 200 is perpendicular to the calf area frame 101. Further, FIG. 5 is a perspective view of an external appearance of a structure of the stopper pin 410 and showing a state in which the stopper pin 410 is insertion-fitted into the holder. Note that while FIG. 4 shows a state in which the cover 340 is removed, FIG. 5 shows a state in which the cover 340 is attached.

FIGS. 4 and 5 show states in which the stopper pin 410 for plantar flexion has not been insertion-fitted yet. Each of the stopper pin 410 for plantar flexion and the stopper pin 420 for dorsiflexion is replaceable (i.e., removable) for the holder 310. The stopper pin 420 has a structure similar to that of the stopper pin 410 and therefore only the stopper pin 410 is explained.

The stopper pin 410 has a bolt-like shape as a whole, and includes, when viewed from its tip, a projecting pin part 411, a locking part 412, a base-axis part 413, and a knob part 415, all of which are arranged so that their central axes are aligned with each other. The projecting pin part 411 functions as a projecting part of the stopper pin 410. Further, the projecting pin part has a cylindrical shape and extends along the central axis. Furthermore, its length is accurately adjusted to a predetermined effective length $L_k$. That is, the effective length $L_k$ corresponds to the projecting length of the projecting part. Further, the end face of the tip of the projecting pin part functions as an impact receiving surface 411a that comes into contact with the swing shaft 320.

In the projecting pin part 411, a groove extending in a circumferential direction that will appear when the impact receiving surface 411a is worn out by an allowable amount or larger due to contact with the swing shaft 320 is preferably formed. That is, a groove extending in the circumferential direction is formed in a place in a trunk part of the projecting pin part 411 that is located a predetermined length (an allowable wearing length) apart from the impact receiving surface 411a. When a user views the stopper pin 410 from the side of the impact receiving surface 411a and observes this groove, he/she can determine that it is time to replace the stopper pin 410. Note that at least the projecting pin part 411 of the stopper pin 410 is preferably made of a metal that is relatively resistant to wearing such as duralumin.

The locking part 412 has a so-called "two-side cut shape" and the width of the narrowest part thereof is roughly equal to the diameter of the projecting pin part 411. The base-axis part 413 includes a cylindrical part connected to the locking part 412 and a two-side cut shape part connected to the knob part 415. A conical positioning hole 414 is formed on a circular-arc surface of the two-side cut shape part.

The knob part 415 is a part that a user grasps when he/she replaces the stopper pin 410 and is, for example, knurled to improve its grasping property. An inscribed mark 416, which is a mark indicating a property of the stopper pin 410, is formed on a top surface 415a, i.e., an end face of the knob part 415. The inscribed mark 416 is provided so that a user can recognize, at a glance, whether the stopper pin is for plantar-flexion or for dorsiflexion, and/or how long the effective length $L_k$ is (or how large the regulated swing angle is).

An insertion-fitting hole 310c, which is formed as a hole when the cover 340 is attached and in which the stopper pin 410 for plantar-flexion is inserted, and an insertion-fitting hole 310e, in which the stopper pin 420 for dorsiflexion is inserted, are formed on a side of the holder 310. Specifically, the insertion-fitting hole 310c is located in a position on a side wall of the holder 310 higher than the swing axis Sa and penetrates (i.e., extends) along the x-axis direction to the internal space in which the swing shaft 320 swings. Similarly, the insertion-fitting hole 310e is located in a position on the side wall of the holder 310 lower than the swing axis Sa and penetrates (i.e., extends) along the x-axis direction to the internal space in which the swing shaft 320 swings.

A locking groove 310d vertically extending along the z-axis direction is formed at or near the middle of the insertion-fitting hole 310c. Similarly, a locking groove 310f vertically extending along the z-axis direction is formed at or near the middle of the insertion-fitting hole 310e.

A user inserts the stopper pin 410 for plantar-flexion into the insertion-fitting hole 310c. Note that by inserting the stopper pin 410 in such a manner that the narrowest part of the locking part 412 is directed in the vertical direction (i.e., the z-axis direction), the locking part 412 reaches the locking groove 310d. When the user rotates the stopper pin 410 around its central axis so that its phase is rotated by 90 degrees at this point, the locking part 412 is locked in the locking groove 310d. At the same time, a tip of a ball-plunger 315 disposed near the side wall of the holder 310 is engaged in the positioning hole 414 and hence the stopper pin 410 is positioned and fixed to the holder 310.

Similarly, the user inserts the stopper pin 420 for dorsiflexion into the insertion-fitting hole 310e. Note that by inserting the stopper pin 420 in such a manner that the narrowest part of the locking part 422 is directed in the vertical direction (i.e., the z-axis direction), the locking part 422 reaches the locking groove 310f. When the user rotates the stopper pin 420 around its central axis by 90 degrees at this point, the locking part 422 is locked in the locking groove 310f. At the same time, a tip of a ball-plunger 316 disposed near the side wall of the holder 310 is engaged in the positioning hole 424 and hence the stopper pin 420 is positioned and fixed to the holder 310.

When the stopper pins 410 and 420 are fixed to the holder 310 as described above, their projecting pin parts 411 and 421 project into the internal space in which the swing shaft 320 swings by lengths corresponding to the effective lengths $L_k$. That is, the projecting pin parts 411 and 421 project in a direction perpendicular to the swing axis Sa of the swing shaft 320. The swing range for plantar-flexion motions is regulated according to the projecting length of the projecting pin part 411 and the swing range for dorsiflexion motions is regulated according to the projecting length of the projecting pin part 421.

Figure 6:
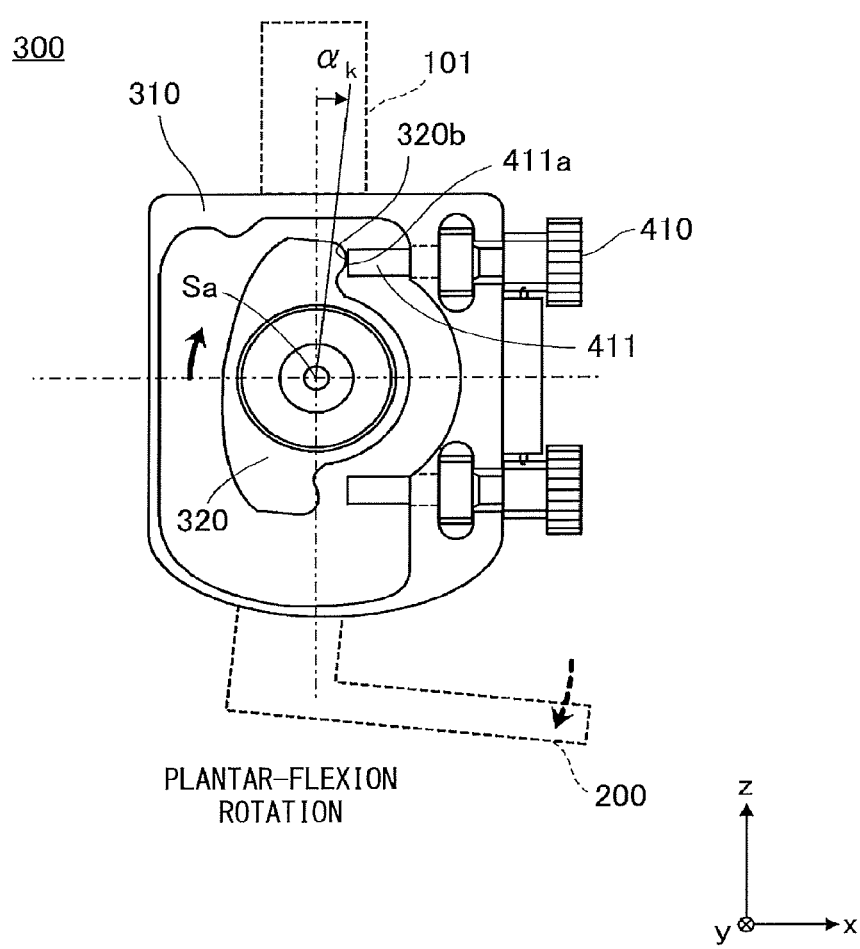
FIG. 6 is a schematic diagram showing a state of a plantar-flexion rotation of a joint mechanism.

FIG. 6 is a schematic diagram showing a state of a plantar-flexion rotation of the joint mechanism 300. The swing shaft 320 includes two arm parts extending in radial directions with respect to the swing axis Sa. An impact surface 320b, which collides with the impact receiving surface 411a, i.e., the surface of the tip of the stopper pin 410, is formed in one of the arm parts. When a wearer performs a plantar-flexion motion, the sole frame 200 swings in a direction indicated by a dotted-line arrow in the figure. As a result, the swing shaft 320 swings in a direction indicated by a bold-line arrow. Then, when the swing shaft 320 swings around the swing axis Sa by $\alpha_k$ degrees, the impact surface 320b collides with the impact receiving surface 411a. That is, the joint mechanism 300 regulates the swing range so that the swing shaft 320 can swing on the plantar-flexion side by $\alpha_k$ degrees or smaller.

The stopper pin 410 for plantar-flexion is selected by a user from a set of a plurality of stopper pins with projecting pin parts 411 having different effective lengths $L_k$ according to the desired regulated swing range on the plantar-flexion side. The impact surface 320b of the swing shaft 320 is processed (e.g., machined) into a cylindrical-surface shape so that the impact surface 320b collides with the impact receiving surface 411a in line contact regardless of which of the stopper pins having different effective lengths $L_k$ is inserted into the insertion-fitting hole 310c.

Specifically, since the impact receiving surface 411a is a flat surface, the impact surface 320b is processed (e.g., machined) so that it has a cylindrical surface with respect to the central axis parallel to the swing axis Sa. Since the impact surface 320b collides with the impact receiving surface 411a in line contact irrespective of the desired regulated swing angle $\alpha_k$, it is possible to disperse an impact force that is caused at the time of a collision and thereby to reduce damage and wear of the stopper pin 410. Note that the set of stopper pins may include a stopper pin having an effective length $L_k$ by which the swing angle $\alpha_k$ on the plantar-flexion side is regulated to 0 degrees.

Figure 7:
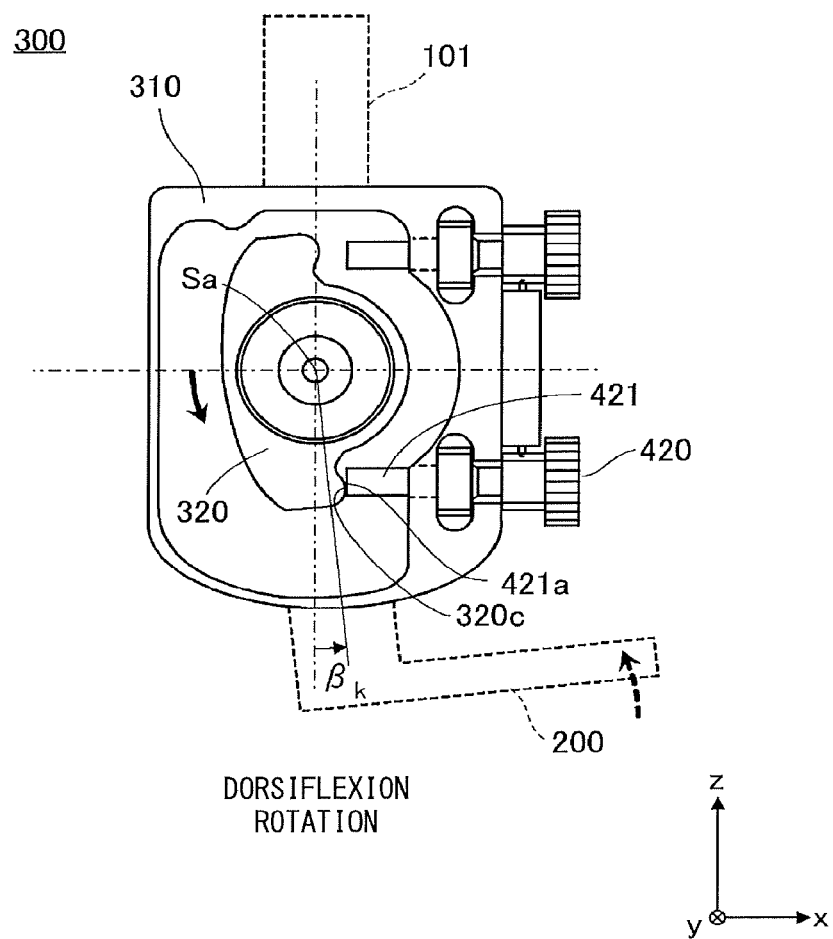
FIG. 7 is a schematic diagram showing a state of a dorsiflexion rotation of the joint mechanism.

FIG. 7 is a schematic diagram showing a state of a dorsiflexion rotation of the joint mechanism 300. In the swing shaft 320, an impact surface 320c, which collides with an impact receiving surface 421a, i.e., the surface of the tip of the stopper pin 420, is formed in the other of the two arm parts extending in the radial directions with respect to the swing axis Sa, i.e., in one of the two arm parts in which the impact surface 320b is not formed. When a wearer performs a dorsiflexion motion, the sole frame 200 swings in a direction indicated by a dotted-line arrow in the figure. As a result, the swing shaft 320 swings in a direction indicated by a bold-line arrow. Then, when the swing shaft 320 swings around the swing axis Sa by $\beta_k$ degrees, the impact surface 320c collides with the impact receiving surface 421a. That is, the joint mechanism 300 regulates the swing range so that the swing shaft 320 can swing on the dorsiflexion side by $\beta_k$ degrees or smaller.

Similarly to the stopper pin 410, the stopper pin 420 for dorsiflexion is selected by a user from a set of a plurality of stopper pins with projecting pin parts 421 having different effective lengths $L_k$ according to the desired regulated swing range on the dorsiflexion side. The impact surface 320c of the swing shaft 320 are processed into a cylindrical-surface shape so that the impact surface 320c collides with the impact receiving surface 421a in line contact regardless of which of the stopper pins having different effective lengths $L_k$ is inserted into the insertion-fitting hole 310e.

Specifically, since the impact receiving surface 421a is a flat surface, the impact surface 320c is processed so that it has a cylindrical surface with respect to the central axis parallel to the swing axis Sa. Since the impact surface 320c collides with the impact receiving surface 421a in line contact irrespective of the desired regulated swing angle $\beta_k$, it is possible to disperse an impact force that is caused at the time of a collision and thereby to reduce damage and wear of the stopper pin 420. Note that the set of stopper pins may include a stopper pin having an effective length $L_k$ by which the swing angle $\beta_k$ on the dorsiflexion side is regulated to 0 degrees. By selecting the stopper pin 410 by which the swing angle $\alpha_k$ on the plantar-flexion side is regulated to 0 degrees and the stopper pin 420 by which the swing angle $\beta_k$ on the dorsiflexion side is regulated to 0 degrees, it is possible to fix the joint angle at a reference position.

As has been explained so far, the joint mechanism 300 can regulate each of the swing angle $\alpha_k$ on the plantar-flexion side and the swing angle $\beta_k$ on the dorsiflexion side to a desired swing range independently of each other by selecting stopper pins 410 and 420 having appropriate effective lengths $L_k$ and fixing the selected stopper pins to the holder 310. In the ankle joint regulation apparatus 10 according to this embodiment, since the swing range is regulated to a range narrower than a range in which a wearer can physically and naturally bend his/her foot as an ankle joint function, the impact surfaces 320b and 320c collide with the impact receiving surfaces 411a and 421a, respectively, with large forces. However, the ankle joint regulation apparatus 10 is configured so that the stopper pins 410 and 420 are replaceable. Therefore, it is possible to accurately maintain the desired regulated swing range by replacing them with new ones according to their worn-out situation or the like. Further, the ankle joint regulation apparatus 10 is configured so that a wearer can easily insert or remove the stopper pins 410 and 420 with one hand without detaching the ankle joint regulation apparatus 10 from the wearer. Therefore, the wearer can proceed with rehabilitation training without a hitch.

Figure 8A:
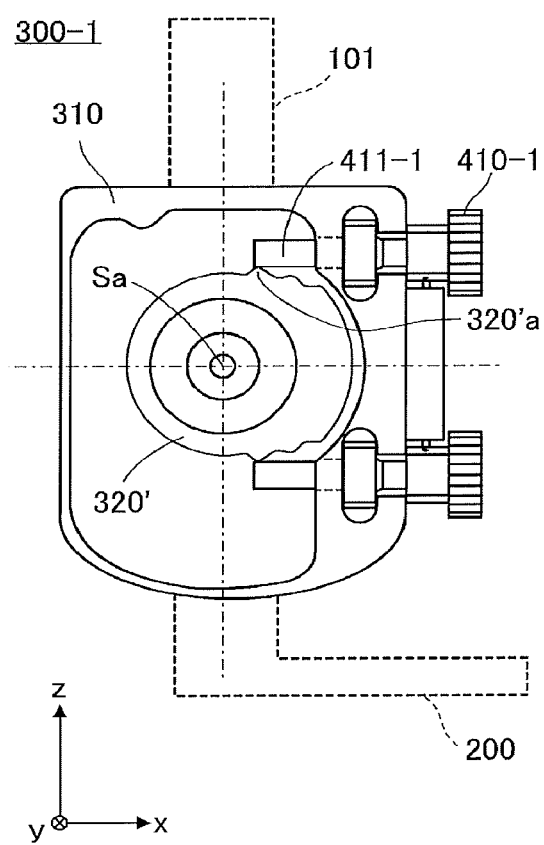
FIG. 8A is a schematic diagram schematically showing a configuration of a joint mechanism and its rotation state according to another embodiment.
Figure 8B:
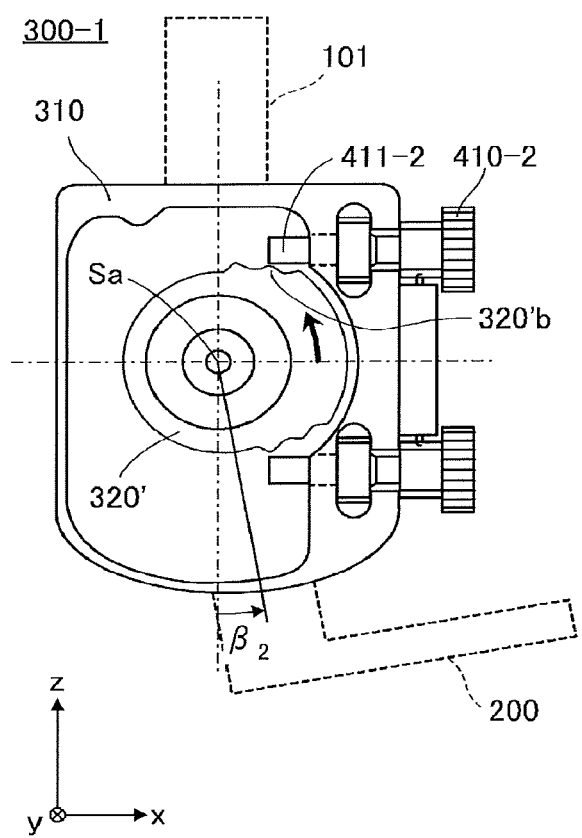
FIG. 8B is a schematic diagram schematically showing a configuration of a joint mechanism and its rotation state according to another embodiment.
Figure 8C:
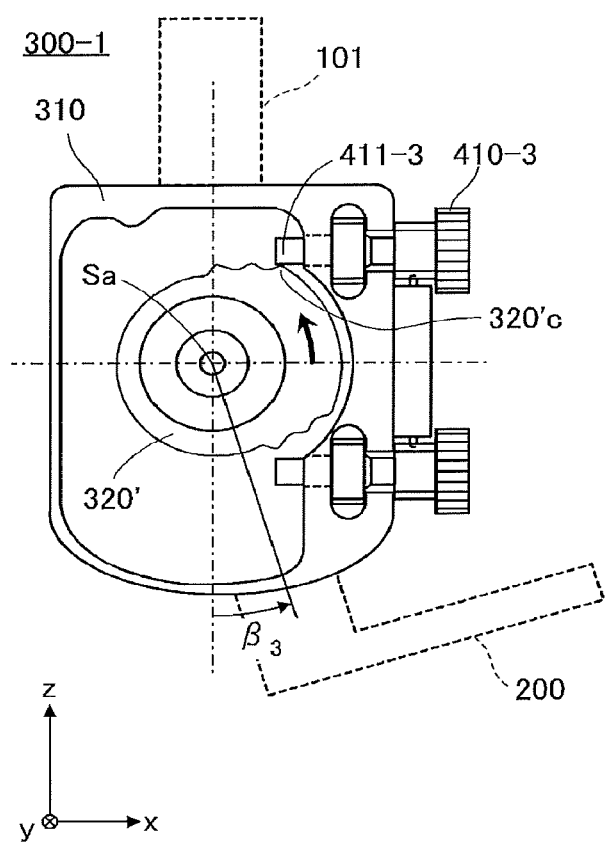
FIG. 8C is a schematic diagram schematically showing a configuration of a joint mechanism and its rotation state according to another embodiment.

Next, several examples according to modified examples of the above-explained joint mechanism 300 are explained. Each of FIGS. 8A to 8C is a schematic diagram schematically showing a configuration of a joint mechanism 300-1 and its rotation state according to another embodiment. The joint mechanism 300-1 differs from the joint mechanism 300 in the shape and the position of the swing shaft. While the swing shaft 320 included in the joint mechanism 300 includes two arm parts extending in radial directions, a swing shaft 320' included in the joint mechanism 300-1 includes only one arm part extending in a radial direction. Further, this arm part extends toward a space formed between the two stopper pins. In each of a top surface and a bottom surface of the arm part, a plurality of projections for regulating a dorsiflexion rotation and a plurality of projection for regulating a plantar-flexion rotation are formed. Since the dorsiflexion rotation and the plantar-flexion rotation have a symmetrical relation with each other, only the dorsiflexion rotation is explained hereinafter while omitting the explanation of the plantar-flexion rotation.

FIG. 8A shows a state in which a stopper pin 410-1 for plantar-flexion having a longest projecting pin part 411-1 is inserted. In this case, among the plurality of projections formed on the top surface of the arm part of the swing shaft 320', a projection 320'a located closest to the swing axis Sa comes into contact with a side of the projecting pin part 411-1, so that the rotation angle of the dorsiflexion rotation is regulated to 0 degrees. In other words, the sole frame 200 does not allow a dorsiflexion motion of the wearer.

FIG. 8B shows a state in which a stopper pin 410-2 for plantar-flexion having a second longest projecting pin part 411-2 is inserted. In this case, among the plurality of projections formed on the top surface of the arm part of the swing shaft 320', a projection 320'b located second closest to the swing axis Sa comes into contact with a side of the projecting pin part 411-2. Therefore, the rotation angle of the dorsiflexion rotation is regulated to $\beta_2$ degrees. In other words, the sole frame 200 allows the wearer to perform dorsiflexion motions in a range from 0 degrees to $\beta_2$ degrees.

FIG. 8C shows a state in which a stopper pin 410-3 for plantar-flexion having a third longest projecting pin part 411-3 is inserted. In this case, among the plurality of projections formed on the top surface of the arm part of the swing shaft 320', a projection 320'c located third closest to the swing axis Sa comes into contact with a side of the projecting pin part 411-3. Therefore, the rotation angle of the dorsiflexion rotation is regulated to $\beta_3$ degrees. In other words, the sole frame 200 allows the wearer to perform dorsiflexion motions in a range from 0 degrees to $\beta_3$ degrees.

Even in the above-described configuration of the joint mechanism 300-1, it is possible to bring the swing shaft 320' into contact with the projection parts of the stopper pints at one end and the other end of the swinging motion of the swing shaft 320' and thereby to regulate its swing range.

Figure 9:
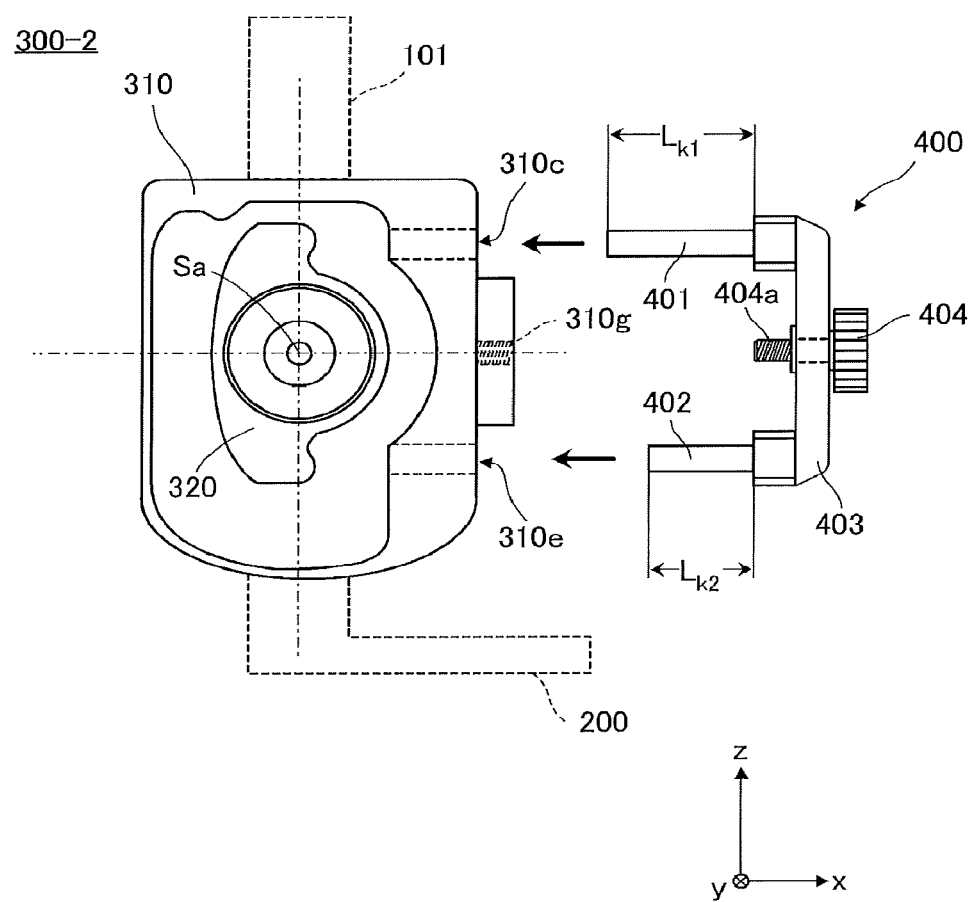
FIG. 9 is a schematic diagram schematically showing a joint mechanism according to another embodiment.

FIG. 9 is a schematic diagram schematically showing a joint mechanism 300-2 according to another embodiment. The joint mechanism 300-2 differs from the joint mechanism 300 in the structure of the stopper pin. While the stopper pin 410 for plantar-flexion and the stopper pin 420 for dorsiflexion are independent of each other in the joint mechanism 300, the joint mechanism 300-2 uses a stopper pin 400 in which a projecting pin part 401 for plantar-flexion and a projecting pin part 402 for dorsiflexion are integrally formed.

The stopper pin 400 is mainly composed of the projecting pin part 401 for plantar-flexion, the projecting pin part 402 for dorsiflexion, a bridge 403 that supports these pin parts at both ends of the bridge, and a fixing screw 404 rotatably supported at the center of the bridge.

An insertion-fitting hole 310c is a straight hole for allowing the projecting pin part 401 for plantar-flexion to be inserted therethrough and an insertion-fitting hole 310e is a straight hole for allowing the projecting pin part 402 for dorsiflexion to be inserted therethrough. How far the projecting pin parts 401 and 402 should project into the internal space in which the swing shaft 320 swings depends on an effective length $L_{k1}$ of the projecting pin part 401 and an effective length $L_{k2}$ of the projecting pin part 402, respectively. That is, as a set of stopper pins 400, a plurality of combinations of different effective lengths $L_{k1}$ and $L_{k2}$ are prepared. A user selects an appropriate combination from the set according to the desired regulated swing range.

By inserting the projecting pin part 401 for plantar-flexion and the projecting pin part 402 for dorsiflexion into the insertion-fitting holes 310c and 310e, respectively, and screwing a screw part 404a of the fixing screw 404 into a screw hole 310g formed in the holder 310, the stopper pin 400 is fixed to the holder 310. When the stopper pin 400 is fixed as described above, the projecting pin parts 401 and 402 function in manner similar to the projecting pin parts 411 and 421, respectively, of the joint mechanism 300. Further, the above-described stopper pin 400 can also be adopted in the joint mechanism 300-1. In such a case, the projecting pin parts 401 and 402 serve as projecting pin parts for dorsiflexion and plantar-flexion, respectively.

Figure 10:
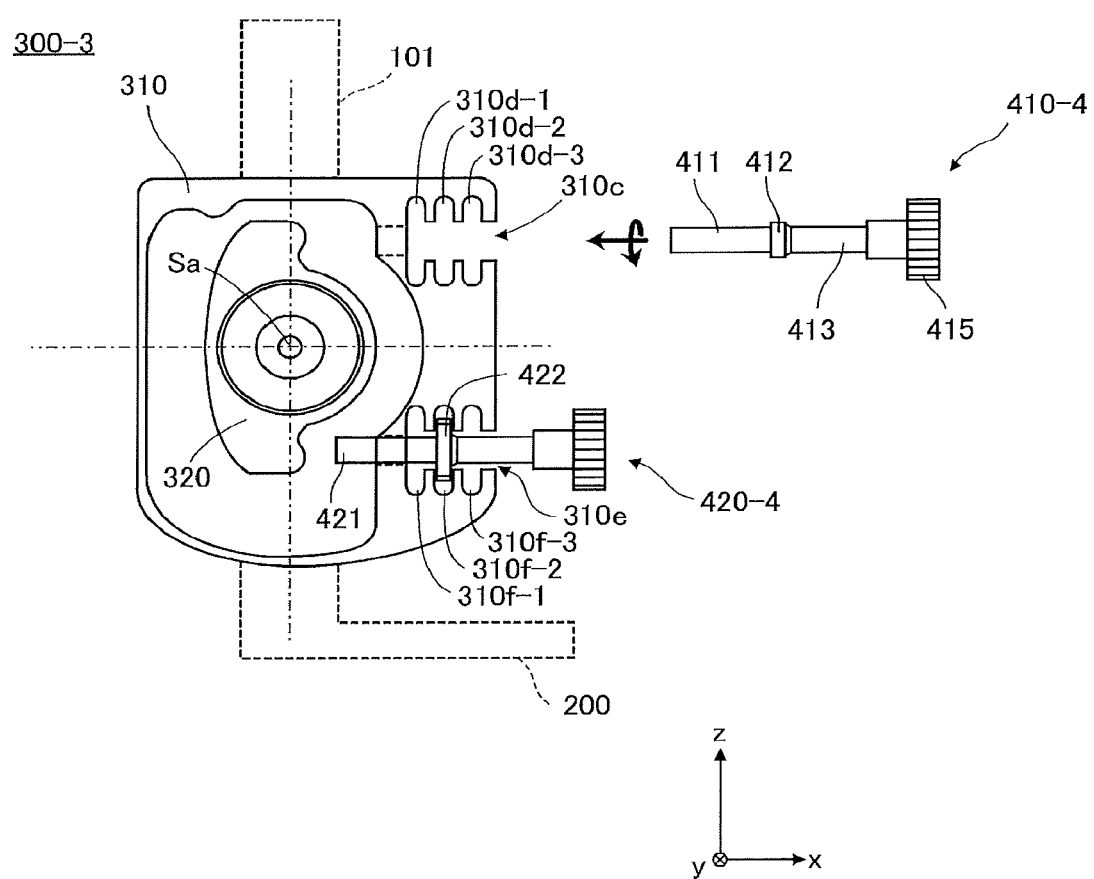
FIG. 10 is a schematic diagram schematically showing a joint mechanism according to another embodiment.

FIG. 10 is a schematic diagram schematically showing a joint mechanism 300-3 according to another embodiment. The joint mechanism 300-3 differs from the joint mechanism 300 in the structure of the stopper pin. While a plurality of stopper pins 400 with projecting pin parts having different effective lengths are prepared according to the desired regulated swing range in the joint mechanism 300, the joint mechanism 300-3 uses a stopper pin including one projecting pin part that functions as a plurality of different effective lengths.

A stopper pin 410-4 for plantar-flexion and a stopper pin 420-4 for dorsiflexion have structures similar to each other. Similarly to the stopper pin 410, the stopper pin 410-4 includes, when viewed from its tip, a projecting pin part 411, a locking part 412, a base-axis part 413, and a knob part 415, all of which are arranged so that their central axes are aligned with each other. However, a cylindrical part of the base-axis part 413 is slightly longer than that of the stopper pin 410.

While one locking groove 310d is formed for the insertion-fitting hole 310c in the joint mechanism 300, three locking grooves 310d-1, 310d-2 and 310d-3 are formed along the hole-axis direction for the insertion-fitting hole 310c in the joint mechanism 300-3. That is, a user can change the projecting length of the projecting pin part 411 by selecting which of the locking grooves the locking part 412 of the stopper pin 410-4 is locked. If the user wants to make the projecting pin part 411 project as much as possible, he/she may lock the locking part in the locking groove 310d-1 formed on the innermost side, whereas if the user wants to make the projecting pin part 411 project as little as possible, he/she may lock the locking part in the locking groove 310d-3 formed on the outermost side. In this way, it is possible to select the regulation angle of the plantarflexion rotation by changing the place where the locking part is locked.

The dorsiflexion rotation can be regulated in a similar manner. Three locking grooves 310f-1, 310f-2 and 310f-3 are formed along the hole-axis direction for the insertion-fitting hole 310e. A user can change the projecting length of the projecting pin part 421 by selecting which of the locking grooves the locking part 422 of the stopper pin 420-4 is locked. In this way, it is possible to select the regulation angle of the dorsiflexion rotation by changing the place where the locking part is locked.

Even in the above-described configuration of the joint mechanism 300-3, it is possible to bring the swing shaft 320 into contact with the projection parts of the stopper pints at one end and the other end of the swinging motion of the swing shaft 320 and thereby to regulate its swing range.

The above-described ankle joint regulation apparatus is explained on the assumption that the regulation member for regulating the swing range is a stopper pin. However, the form of the regulation member is not limited to the stopper pin. Instead of using the pin-shaped member, a block-shaped member may be used. In the above-explained embodiments, an ankle joint regulation apparatus attached to an ankle joint, in which relatively large impacts occur in both ends of the regulated swing range, is explained. However, use of the above-described joint mechanism is not limited to use for ankle joint regulation apparatuses. That is, the above-described joint mechanism can be used for joint regulation apparatuses used for any kinds of joints, provided that the joint mechanism supports a first member attached to a part of a body located on a side of one of bones and a second member attached to a part of the body located on a side of the other bone so that they can swing in a regulated swing range. Further, the relative rotation of the first and second members may be assisted by an actuator such as a motor.

An aspect of the above-described ankle joint regulation apparatus is summarized. A joint regulation apparatus configured to regulate a movable range of a joint connecting a first bone part of a wearer with a second bone part of the wearer, including: a first member configured to be attached to a part of a body located on the first bone side; a second member configured to be attached to a part of the body located on the second bone side; and a joint mechanism configured to support the first and second members so that the first and second members can swing with respect to each other along a movable direction of the joint, in which the joint mechanism includes: a holder integrally provided with the first member; a regulation member including a projection part formed on a tip side, the regulation member being configured to be insertion-fitted into the holder in a replaceable manner; and a swing member configured to swing in an integrated manner with the second member, the swing member being further configured to come into contact with the projecting part of the regulation member at at least one of one end and the other end of a swinging motion, so that its swing range is regulated.

From the invention thus described, it will be obvious that the embodiments of the invention may be varied in many ways. Such variations are not to be regarded as a departure from the spirit and scope of the invention, and all such modifications as would be obvious to one skilled in the art are intended for inclusion within the scope of the following claims.

What is claimed is:

1. A brace comprising;
a first member configured to be attached to a part of a body located along a first bone part of a wearer, the first member including a calf frame configured to be attached to a calf of the wearer;
a second member configured to be attached to a part of a body located along a second bone part of the wearer, the second member including a sole plate adapted for receiving a sole of the wearer; and
a joint mechanism configured to support the first and second members so that the first and second members can rotate with respect to each other around a rotation axis, wherein
the brace further comprises an insertion-fitting member configured to be insertion-fitted into the joint mechanism in such a manner that the insertion-fitting member can be fixed to and removed from the joint mechanism,
the first member is a member adapted for placing on a calf area of the wearer,
the second member is a member adapted for placing on a foot area of the wearer,
the joint mechanism comprises:
an insertion-fitting receiving part integrally provided with the first member, the insertion-fitting receiving part being configured to enable the insertion-fitting member to be insertion-fitted into the joint mechanism:
a regulation part integrally provided with the second member, the regulation part including a swing shaft and being disposed around the rotation axis in the second member; and
a ball-plunger configured to stop the insertion-fitting member in a predetermined phase when the insertion-fitting member is rotated,
the regulation part, which rotates around the rotation axis in an integrated manner with a rotation of the second member, comes into contact with the insertion-fitting member fixed to the insertion-fitting receiving part on a trajectory of the rotation of the regulation part, so that a range of the rotation of the second member is regulated,
the insertion-fitting member, which is insertion-fitted into the insertion-fitting receiving part, is selected from a set of a plurality of insertion-fitting members according to a desired regulated rotation range, the plurality of insertion-fitting members comprising projecting parts configured to come into contact with the regulation part, the projecting parts having projecting lengths different from each other,
the insertion-fitting receiving part is configured to be an insertion-fitting hole having a plurality of locking grooves, and
the insertion-fitting member comprises a locking part configured to be locked in either of the plurality of locking grooves of the insertion-fitting receiving part when the insertion-fitting member is inserted into the insertion-fitting receiving part and then rotated around a rotation axis parallel to an insertion-fitting direction.

2. The brace according to claim 1, wherein the insertion-fitting member is able to be insertion-fitted into the insertion-fitting receiving part in a state in which the first and second members are already attached to the wearer.

3. The brace according to claim 1, wherein the insertion-fitting member comprises:

a first insertion-fitting member comprising a first projecting part configured to come into contact with the regulation part at one end of a rotating motion thereof; and a second insertion-fitting member comprising a second projecting part configured to come into contact with the regulation part at the other end of the rotating motion thereof.

4. The brace according to claim 3, wherein the projecting length of the first projecting part differs from the projecting length of the second projecting part.

5. The brace according to claim 1, wherein the projecting part of the insertion-fitting member, which comes into contact with the regulation part, projects in a direction perpendicular to the rotation axis of the regulation part, and a contact part of the regulation part, which comes into contact with the projecting part, forms a cylindrical-surface shape so as to come into contact with the projecting part in a straight line parallel to the rotation axis.

6. The brace according to claim 1, wherein for the joint mechanism, the rotation range is determined so that a range of a plantar-flexion motion and a dorsiflexion motion adapted for an ankle joint of the wearer is regulated.

7. The brace according to claim 1. wherein the insertion-fitting member is configured to be insertion-fitted into the insertion-fitting receiving part in a replaceable manner.

8. The brace according to claim 3 wherein the first insertion-fitting member is configured to he insertion-fitted into the insertion-fitting receiving part so as to be entirely disposed above the rotation axis, and the second insertion-fitting member is configured to be insertion-fitted into the insertion-fitting receiving part so as to be entirely disposed below the rotation axis.

* * * * *